United States Patent [19]

Capiau et al.

[11] Patent Number: 5,578,308

[45] Date of Patent: Nov. 26, 1996

[54] GLUTARALDEHYDE AND FORMALIN DETOXIFIED BORDETELLA TOXIN VACCINE

[76] Inventors: Carine Capiau, 5 rue Astrid, B-7022 Harveng (Mons); Jean Petre, Avenue Ch. Lemaire 26, B-1160 Bruxelles, both of Belgium

[21] Appl. No.: 338,361

[22] Filed: Nov. 14, 1994

Related U.S. Application Data

[60] Division of Ser. No. 910,038, filed as PCT/EP91/00257, Feb. 7, 1991, publsihed as WO91/12020, Aug. 22, 1991, abandoned, which is a continuation-in-part of Ser. No. 479,098, Feb. 12, 1990, abandoned.

[51] Int. Cl.$^6$ .................. A61K 39/10; A61K 39/385; C07K 14/235; C07K 17/00

[52] U.S. Cl. .................. 424/240.1; 424/236.1; 424/197.11; 530/403; 530/404; 530/405; 530/406; 530/409; 530/410

[58] Field of Search .................. 530/403–406, 530/377, 409, 410; 424/240.1, 236.1, 197.11

[56] References Cited

U.S. PATENT DOCUMENTS

| | | | |
|---|---|---|---|
| 3,983,229 | 9/1976 | Relyveld et al. | 424/92 |
| 4,070,454 | 7/1978 | Relyveld et al. | 424/89 |
| 4,075,321 | 5/1978 | Relyveld et al. | 424/92 |
| 4,788,058 | 11/1988 | Parton et al. | 424/92 |
| 4,849,358 | 7/1989 | Chazono et al. | 435/252.1 |
| 4,888,169 | 12/1989 | Brown et al. | 424/92 |
| 4,996,299 | 2/1991 | Ginnaga et al. | 530/409 |
| 4,997,915 | 3/1991 | Tan et al. | 530/396 |

FOREIGN PATENT DOCUMENTS

| | | | |
|---|---|---|---|
| 0047802 | 3/1982 | European Pat. Off. | C07G 7/00 |
| 0121249 | 10/1984 | European Pat. Off. | A61K 39/10 |
| 202947A | 11/1988 | European Pat. Off. | |

OTHER PUBLICATIONS

R. K. Gupta et al., J. of Biol. Stand. (1987) 15, 159–164.

A. C. Wardlaw et al., J. med. Micro. Bio., (1976) 9, 89–100.

Munoz et al., Infect. Immunity, (1981) 32, 243–250.

Weiss et al., Ann. Rev. Microbiol., 40:661 (1986).

Habeeb (1969) "A Study of the Antigenicity of Formaldehyde–and Glutaraldehyde–Treated Bovine Serum Albumin and Ovalbumin–Bovine Serum Albumin Conjugate" J. Immunol 102(2):457–465.

Habeeb (1987) "*Schistosoma Mansoni:* Chemical Stabilization of Cercariae by Aldehydes" Exptl. Parasitol. 64:111–119.

Gupta et al (1987) "The Effects of Different Inactivating Agents on the Potency, Toxicity and Stability of Pertussis Vaccine" J. Biol. Stand. 15:87–98.

Andreescu et al (1980) "Comparative Studies of Pertussis Vaccine Batches Inactivated with Glutaraldehyde, β–Propiolactone, Formaldehyde or Thimerosal" Arch. Roum. Path. Exp. Microbiol. 38(3–4):299–308.

Davis et al (1974) "Retention of Significant Antibody Binding by Surface Antigens of Feline Leukemia Cells (FLA) After Fixation with Formaldehyde and Glutaraldehyde" Immunol. Commun. 3(2):189–196.

Kongsvik et al (1974) "Studies on the Red Cell and Antibody–Reactive Sites of the Parvovirus H—1: Effect of Fixatives" Proc. Soc. Exptl. Biol. Med. 145:763–770.

*Primary Examiner*—Kay K. A. Kim

[57] ABSTRACT

A detoxified *B. pertussis toxin* or antigenic preparation is described, which is characterized by stability to reversion to toxicity upon storage at 4°–8° C. and at temperatures above 23° C. Also provided are methods for producing detoxified pertussis toxin and vaccines containing same.

8 Claims, No Drawings

GLUTARALDEHYDE AND FORMALIN DETOXIFIED BORDETELLA TOXIN VACCINE

This is a continuation of application Ser. No. 07/910,038, filed as PCT/EP91/00257, Feb. 7, 1991, published as WO91/12020, Aug. 22, 1991 now abandoned, which is a continuation-in-part of Ser. No. 07/479,098, filed Feb. 12, 1990 now abandoned.

TECHNICAL FIELD

The present invention relates generally to a process for detoxifying or toxoiding a toxic antigen from a selected pathogen in a form safe for use as a human vaccinal agent. More specifically, the invention provides a method for detoxifying pertussis toxin and using the resulting toxoid as a component in a vaccine for *Borderella pertussis*.

BACKGROUND OF THE INVENTION

Whooping Cough, or pertussis, is a highly infectious disease which primarily affects children. In addition to causing respiratory complications, whooping cough may result in nerve damage and high mortality, particularly in children in low socioeconomic groups and in newborn infants without maternal anti-pertussis antibodies. The etiologic agent of pertussis is the gram negative coccobacillus *Bordetella pertussis*. The bacteria are believed to invade the respiratory tract and induce a toxic state which remains even after the disappearance of the bacteria.

Although world health organizations presently recommend the immunization of infants to prevent the incidence and spread of pertussis, great concern has arisen over the negative effects of various vaccine forms. The toxicity of conventional *B. pertussis* vaccine formulations causes side effects which vary from simple flushing to permanent neurological damage and/or death. Consequently, reduced use of conventional *B. pertussis* vaccines has resulted in re-explosion of the incidence of pertussis cases. The most widely used vaccine contains whole *B. pertussis* organisms which are inactivated after treatment at 56° C. for 30 minutes. Since the bacteria are not subjected to any detoxification treatment, any toxic substance which can withstand the elevated temperature is included in the vaccine and contributes to the occurrence of side effects. Another consequence of this type of vaccine is the formation of a broad spectrum of antibodies as a response upon administration. The sera induced by such vaccines lack high specificity and high protecting potential for use as preventive or therapeutic treatments, and have no value at all as diagnostic materials.

The most important methods for detoxifying pathogens for vaccine use are heat and chemical treatment with formaldehyde or glutaraldehyde. However, variabilities in cultivation of culture supernatant of *B. pertussis* allow the final composition of the microorganism to vary, and the deactivating agents, glutaraldehyde or formaldehyde, occasionally lead to aggregated materials subject to conversion to active toxic substances upon storage.

For example, U.S. Pat. No. 3,983,229 by Relyveld relates to a process for preparing vaccines by contacting a virus with glutaraldehyde at a concentration between 0.00131M to 0.0526M for between one and three hours. This process occurs at temperatures between 35° and 40° C. and the reaction may be stopped by the addition of an agent able to block glutaraldehyde or react with glutaraldehyde in its free state. The blocking agent can be an amino acid or an inorganic salt. U.S. Pat. No. 4,070,454 by Relyveld discloses another process for preparing a viral vaccine which involves inactivating the virus with glutaraldehyde at a concentration of 0.00263M for between 1.5 hours to about 5 days. U.S. Patent No. 4,075,321 further improves this process for inactivating bacterial toxins by reacting whole bacteria with glutaraldehyde at a concentration of from about 0.00131 to 0.0526M.

Gupta, *J. Biol. Stand.*, 15:159–164 (1987) compares whole cell vaccines obtained via the classical heat treatment with those obtained via Relyveld's method of glutaraldehyde detoxification reaction. Both types of vaccine clearly lose 30 to 50% of their potency upon storage at 35° C. for 30 days. Further, these preparations have important disadvantages when compared with more recently developed acellular or component vaccines, e.g., low immunogenicity and serious side effects caused by residual toxicity upon administration. These vaccines have proven to be much less protective than those prepared from virulent strains. See Wardlaw et al, *J. Med. Micro. Biol.*, 9:89–100 (1976).

To avoid the side effects caused by whole virus vaccines, research turned to the investigation of the toxic components of the *B. pertussis* bacteria for use in acellular and component vaccines. One important *B. pertussis* antigen is pertussis toxin (PT), a protein exotoxin which plays a major role in the pathogenesis of whooping cough and is believed to be the major protective antigen of *B. pertussis* [A. A. Weiss et al, *Ann. Rev. Microbiol.*, 40:661 (1986)]. PT induces various serious biopathological changes, whether present alone or as a contaminant of other antigenic factors from this organism, at such a low amount that it impedes the administration of *B. pertussis* cells or cell extracts as vaccine components in amounts sufficient to provide a good level of protection. Therefore, *B. pertussis* cells or cell extracts must be detoxified prior to their use in a vaccine preparation.

For the detoxification of PT (or of an acellular or component vaccine mixture containing PT), three major methods have been described. In European patent application publication No. 121249A the hemagglutinin fraction, purified from a *B. pertussis* culture supernatant and containing PT, is detoxified with formalin in the presence of an amino acid, and subsequently used for the formulation of a vaccine. The immunogenicity and the degree of detoxification reached are excellent, but the toxicity restores partially upon storage of the vaccine preparation at 37° C. for 30 days.

Munoz, *Infect. Immunol.*, 32:243–250 (1981) applied a detoxification method analogous to the one of Relyveld to PT, but in the presence of salt. After two hours incubation at room temperature in the presence of 0.05% glutaraldehyde, subsequent addition of lysine up to 0.02M and another two hours of incubation, and final dialysis, an anatoxin with high immunogenicity was produced. This anatoxin was stable; its toxicity did not restore after 30 days storage at 37° C.

However, the degree of detoxification was lower than obtained with the formalin/amine acid method.

In European patent application publication No. 202947A carbodiimides are presented as efficient reagents for the detoxification of PT and *B. pertussis* fractions containing PT. However, the toxoids obtained are not stable upon 30 day storage at 37° C.

There thus remains a continuing need in the art for effective and safe vaccines against whooping cough which retain their activity and do not revert to toxicity upon storage.

SUMMARY OF THE INVENTION

As one aspect, the present invention provides a method for the detoxification of a selected toxic antigen from a pathogenic microorganism. The method of the present invention involves the steps of partially detoxifying the selected toxin or a composition containing the toxic antigen with glutaraldehyde, followed by reacting the partially detoxified toxin with formalin in the presence of selected amino acids. The resulting toxoid or toxoid-containing preparation is stable against reversion to toxicity under the influence of temperatures above about 23° C. i.e., room temperature.

One exemplary antigen employed to illustrate the use of this method is the *B. pertussis* toxin. Other toxins which may be subjected to the method of this invention include, for example, tetanus toxin or diphtheria toxin. This method can be used to inactivate the toxin, e.g., pertussis toxin (PT), which is present as a primary component or only as a contaminant in preparations containing antigenic factors which are non- toxic alone, e.g., the other *B. pertussis* antigens FHA, 69K and agglutinogens. The method of this invention can reduce the toxicity associated with the presence of the selected toxin alone or in compositions of other antigenic factors of the same pathogen to suitable levels for use in vaccine formulations.

As another aspect, this invention provides detoxified pertussis toxin that is stable to reversion to toxicity at temperatures of 23° C. or above. This toxoid of the invention is also characterized by a high degree of immunogenicity, as is demonstrated by the ability of the toxoid to induce neutralizing antibodies. The presence of neutralizing antibody is detected by specific assays, i.e., histamine sensitization of mice or clustering of Chinese Hamster Ovary cells. The detoxified toxins of this invention are stable enough to preserve immunogenicity for more than a month under adverse storage conditions at 37° C. These toxoids are useful starting materials for the composition of high quality *B. pertussis* vaccines, and may also be used for mixed vaccines, or for the preparation of hyperimmune sera.

As another aspect of the present invention, there are provided compositions of *B. pertussis* antigenic factors, e.g., filamentous hemagglutinin (FHA), the 69K factor or other *B. pertussis* agglutinins, which are useful for the preparation of vaccines to the organism and which contain at least trace amounts of detoxified PT toxin as above-described.

In still a further aspect, vaccines against *B. pertussis* infection are provided which remain stable at temperatures of up to 56° C. and do not require special cold shipping and delivery conditions. The vaccines of this invention are characterized by easy maintenance and storage under less than optimal conditions. The vaccines developed using the toxoids of the present invention enable vaccination programs to be executed in isolated or poorly developed regions, where cold storage conditions normally required for the maintenance of other toxoided vaccines is unavailable and atmospheric conditions are extreme. Even in such conditions the vaccines of this invention are stable, and of high quality.

Still a further aspect of this invention is a method for preparing mono- or multifunctional vaccines incorporating an effective amount of the toxoids of the present invention. Other aspects and advantages of the present invention are described further in the following detailed description thereof.

DETAILED DESCRIPTION OF THE INVENTION

The present invention provides a method for detoxifying selected pathogenic toxic antigens, e.g., *B. pertussis* toxin, for use in vaccine formulations, improved vaccine formulations containing the selected toxoid and the preparations containing the toxoided antigen.

It is reasonably expected that the method of the present invention is capable of toxoiding a number of toxic antigens from a variety of pathogenic microorganisms for which vaccines are desirable, e.g., tetanus toxin or diphtheria toxin, among others. However, for ease of description and experimentation, the pertussis toxin from the pathogen *Borderella pertussis* is employed herein to illustrate the efficacy of this toxoiding method.

Briefly described, the toxoided PT of this invention is produced by partially detoxifying the toxin using glutaraldehyde as a reagent and then reacting the PT with formaldehyde in the presence of amino acids.

According to this invention, extracts of PT are obtained from a fermentation broth or culture of *Bordetella pertussis*. Various strains of *B. pertussis* for use in the methods of this invention are described and readily available in commercial collections, such as the American Type Culture Collection, Rockville, Md. Any of these available strains may be used in the processes of the present invention, provided they are capable of producing the desired antigenic factor, PT, in adequate amounts in a liquid culture medium.

Examples of strains that may be employed in the present invention include, without limitation, *B. pertussis* phase I, *B. pertussis* phase II, *B. pertussis* phase I CS, *B. pertussis* Tohama, *B. pertussis* strain 185-30, *B. pertussis* strain 18-323, *B. pertussis* strain 134, *B. pertussis* strain 509, *B. pertussis* strain Wellcome 28, and Office of Biologics *B. pertussis* strain 165. A preferred strain for use in the present invention is *B. pertussis* phase I, Tohama, which is available from the Institute of Fermentation, Osaka, Japan, under accession number IFO-14073.

For use in the present invention the selected *B. pertussis* strain can be grown in a variety of ways known to one of skill in the art. Various cultivation methods are known which employ different cultivation steps, and liquid or solid media, depending on the quantity and origin or conservation method of the seed culture. However, any known method will suffice for use in the present invention which provides an inoculum of an conventionally acceptable size for large scale production.

A suitable medium for growth of a *B. pertussis* inoculum may be selected by one of skill in the art including, without limitation, Gengou medium [European patent No. 0 077 646; the media described in N. Andorn et al, *Appl. Microbiol. Biotechnol.*, 28:356–360 (1988) and references cited therein; Verway medium [U.S. Pat. No. 4,784,589]; synthetic medium B2 [P. Van Hemert, in. *Proq. Indust. Microbiol.*, (Bull, M. J., ed), vol. 13, p.151, Elsevier Sci., Amsterdam (1977)] or described modifications thereof.

For growth of the *B. pertussis* culture, which is the starting material of the present invention, an inoculum is added to a suitable liquid medium and fermentation is conducted employing conventional fermentation methods and fermentor designs known in the art. Those of skill in the art will appreciate that different results may be obtained depending upon the selection of a particular combination of conventional fermentor design, fermentation medium, method and parameters. Preferred combinations for use in the present invention are those suitable for use in large-scale production. Examples of such combinations of methods, designs and media are exemplified in European patent application publication No.A 077,646; European patent application publication No.A 121,249; European patent application publication No.A 239,504; Andorn et al, Sato et al (1983), Sekura et al and Svoboda et al, all cited above. The methods described in European patent application publication No.A 121,249; Andorn et al, cited above, and European patent application No.A 239,504 are most preferred.

In the practice of this invention, after completion of fermentation, the *B. pertussis* fermentation broth is maintained in a sterile condition to avoid denaturation and/or degradation of the desired PT factor. In a preferred embodiment of the invention the broth is cooled to 1°–10° C. and held at this temperature. The pH is adjusted to below 7.0. Preferably the pH is adjusted to a range of between about pH 6.0 and pH 6.4 with phosphoric or acetic acid. A preservative can optionally be added, e.g., sodium thimerosal to a final concentration of up to 0.2 g/l or 2-phenoxy-ethanol up to a final concentration of between 0.5% to 1%, to the broth. If desired, a preservative may be also added to the buffer solutions used in the processes of this invention.

As an optional first step in the method of the invention, the fermentation broth can be passed over a filter to remove major particles and pellets therefrom, provided that contact is avoided with contamination risks from the environment. The resulting broth may be subjected to the following steps of the method. Alternatively, a more purified solution containing PT may be treated by the following steps. For ease of explanation, the method will refer to an "antigenic factor solution", which is defined as a preparation containing PT and optionally other *B. pertussis* antigenic factors, such as FHA. This preparation can include fermentation broth containing primarily PT, or a purified solution containing primarily other *B. pertussis* antigens with only contaminating amounts of PT.

According to the method of this invention the antigenic factor solution is diluted to a toxin concentration of approximately 0.02 to 2 mg/ml, preferably 0.1 to 0.25 mg/ml, in an aqueous medium buffered to approximately neutral pH, i.e., pH 5 to about pH 9. Preferably the pH range is 7.5–7.7. A desirable aqueous buffer for this dilution is phosphate buffered saline (PBS). An exemplary buffer contains 50 mM phosphate and 0.5M NaCl, and is referred to herein as Buffer D.

After dilution, the solution may be optionally sterilized by filtration, e.g., through a 0.22 micron sterile membrane. The antigenic factor solution is treated with from 0.03 to 0.07% of a 25% aqueous solution of glutaraldehyde by weight. More preferably, a dilution containing 0.55% of the aqueous 25% glutaraldehyde solution is employed in this treatment step. For purposes of this step the 0.55% by weight glutaraldehyde is preferably present in the buffer D described above.

The glutaraldehyde solution is applied to the antigenic factor solution for approximately 1 to 4 hours. More preferably a range of 1 to 3 hours is employed in the glutaraldehyde treatment step, with a presently preferred time of 2 hours. The temperature of the glutaraldehyde treatment step is desirably ambient temperature, between approximately 20° C. to 25° C. Optionally, shorter reaction times can be used in combination with higher than ambient temperatures, or longer times can be used with lower than ambient temperatures. Inactivation can also be obtained at different reaction temperatures and adequately modified contact times, for example, a temperature of 10° C. may be used for 2 to 8 hours, more preferably for 4 hours. A temperature of 30° C. may be employed for 30 minutes to 2 hours, more preferably 1 hour. Alternatively a temperature of 37° C. may be used for between 15 minutes to 1 hour, more preferably 30 minutes. This glutaraldehyde treatment step may result in partial detoxification of the antigenic factor depending on the time of reaction and concentration of reagents. For example, glutaraldehyde treatment at the concentration described above for 2 hours at 20°–25° C. yields a reduction to 0.003% of the toxic activity. The other treatment conditions may result in a greater reduction of toxic activity.

After this detoxification step, at least one selected amino acid is added to the partially detoxified antigenic factor in the solution. The amino acid is added to a final concentration of approximately 0.05 to 2% by weight. Preferred concentrations of the amino acid is 0.8% by weight.

The selected amino acids for use in this step may include tryptophan, glycine, lysine and derivatives thereof or other amino acids such as those present in protein hydrolyzates. Preferably the amino acids are tryptophan, lysine and glycine or derivatives thereof. The amino acids are preferably prepared in solution, e.g., in the Buffer D described above and may be added to the antigenic factor solution separately or as a mixture of two or more amino acids. In one presently preferred embodiment, three solutions are prepared in Buffer D which contain, respectively, 10% (w/v) Tween® 80 solution, 33 ml of 57.4 mM N-acetyl-tryptophan and 11 ml of 2.2M glycine. These three solutions are sterilized by filtration through a 0.22 micron sterile membrane.

The formalin is added to the antigenic factor and amino acid solution in a concentration of between 1 and 10% by weight, and more preferably 2–4% by weight. The formalin may also be prepared in Buffer D or a like buffer. The formalin is added to the antigenic factor/amino acid solution in approximately equivalent amounts over a period of between 3 to 10 days, more preferably 7 days. During the formalin treatment, the toxins are maintained at a temperature of between 37° to 45° C. In a preferred embodiment the toxins are maintained at between 39° to 41° C. during this step. Preferably the toxins are also agitated periodically during this period and kept under sterile conditions. At the end of the formalin/amino acid treatment step the detoxified *B. pertussis* toxoid solution can be stored at low temperatures, preferably between 2°–6° C. overnight. Any aggregates formed during the detoxification process are then destroyed by subjecting the toxoid to ultrasonication. For example, the solution may be subjected to sonication at a frequency of about 16–80 KHz with a power of up to 1000 watts for a time of 1–30 seconds. Preferably the sonication involves a frequency of about 20 KHz. The range of power may more preferably be between 600–800 watts. The sonication time is preferably between 5 to 15 seconds. The resulting solution is filtered, preferably through a 50 micron screen.

As a final step in the detoxification method of this invention, the incubated product is dialyzed against PBS in a conventional manner to remove any excess reagents. Changes of the dialysis buffer and the duration of dialysis are performed a sufficient number of times to provide that the residual formalin concentration is below 200 ppm. More preferably, the formalin concentration is kept about 20 ppm. This concentration is sufficient to reduce the concentration of other agents used in the inactivation procedure to non-detectible or insignificant concentrations.

The resulting purified *B. pertussis* toxin or mixture of other *B. pertussis* antigenic factors containing PT toxoided by the method of this invention is characterized by complete and irreversible inactivation of toxicity. This stability against reversion to a toxic form is maintained even under conditions of storage in which the temperature is above room temperature, about 23° C. Such stability has been demonstrated in experimental tests for at least one week at 56° C. and for at least four weeks at 37° C. Additionally, the toxoids of the invention are expected to remain stable for more than two years at cold storage temperatures of between 4° to 8° C. This resulting toxoid or antigenic factor may then be employed as a component in *B. pertussis* antigen preparations which may be distributed for later preparation of vaccines or in vaccine formulations.

Therefore, this invention also provides vaccines which contain an immunoprotective quantity of the toxoids or antigenic factors of the invention, i.e., enough of the toxoided PT or other antigenic factors are administered to elicit a protective antibody response against *B. pertussis* infection without serious side effects. Such vaccines may be prepared by conventional techniques. For example, a vaccine for stimulating protection against *B. pertussis* infection in humans may contain stable toxoids and antigenic factors described above and a suitable conventional carrier. One or more of the toxoids or antigenic factors of this invention may be in an aqueous solution buffered at physiological pH for direct use. Alternatively, the toxoided antigens can be admixed or adsorbed with a conventional adjuvant, such as aluminum hydroxide or aluminum phosphate. Such a *B. pertussis* toxoid may also be combined with other immunogens to prepare combination or multi-functional vaccines capable of inducing protection against more than one pathogen. See, e.g., *New Trends and Developments in Vaccines*, eds. Voller et al, University Park Press, Baltimore, Md. (1978).

Such vaccines can be administered by an appropriate route, e.g., by the subcutaneous, intravenous or intramuscular routes. The amount of the selected toxoid of the invention present in each vaccine dose is selected by the attending physician with regard to consideration of the patient's age, weight, sex, general physical condition and the like. The amount to induce an immunoprotective response in the patient without significant adverse side effects may vary depending upon the immunogen employed and the optional presence of an adjuvant. Generally, it is expected that each dose will comprise 2 to 50 ug of antigen, preferably 5 to 25 ug each of toxoid and antigenic factor. Initial doses may be optionally followed by repeated boosts, where desirable. The following examples illustrate the methods of preparing an exemplary toxoid of the invention, and assessments of its immunogenicity and resistance to reversion to toxicity during storage. Also illustrated is an exemplary vaccine preparation employing the toxoid of this invention.

EXAMPLE 1

Toxoiding Method

*B. pertussis* toxin was extracted and purified from fermentor growth cultures as described in European Patent Application Publication No. EP-A-0 352 250 which is incorporated herein by reference. One liter of the purified PT toxin was first treated at room temperature, e.g., 25° C. with 100 ml of a 0.55% (w/v) glutaraldehyde solution prepared in Buffer D. The solution is diluted to a final protein concentration of 0.2 mg/ml in Buffer D described above at neutral pH and is sterilized and filtered through a 0.22 micron sterile membrane. The glutaraldehyde treatment step is allowed to react for 2 hours. Then 4.4 ml of a 10% (w/v) Tween® 80 solution, 33 ml of 57.4 mM N-Acetyl-Tryptophan and 11 ml of 2.2M Glycine were added. These 3 solutions were prepared in the D buffer and sterilized by filtration through a 0.22 micron sterile membrane. Formalin, a 3.7% (w/v) solution in D buffer, was then added in 3 portions according to the following scheme: On the first day, 33 mls; on the second day, 33 mls; and on the third day 22 mls of formalin was added. The final formalin concentration was 0.26% (w/v). During the seven day formalin treatment, the PT toxin was maintained at 40° C.±1° C. under agitation and sterile conditions. At the end of the process, the detoxified PT bulk solution was stored overnight at 2°–6° C. before sonication. The solution was subjected to ultrasonication and the resulting antigen solution was filtered through a 50 micron screen.

EXAMPLE 2

Toxic Properties of the Vaccine Component

The toxoid preparation of Example 1 is compared with products prepared by toxoiding with glutaraldehyde alone, with formalin and amino acids only and with glutaraldehyde and formalin/amino acids as described herein to demonstrate the advantages of the products and methods of this invention.

A study of residual toxicity of the toxoids was conducted after each sample was stored for 1 month at either 4° C. or 37° C. The study included an examination of Chinese hamster ovary (CHO) cell morphology, in which cells exposed to active PT form clusters readily distinguishable from normally growing cells by one skill in the art. See, e.g., Gillenius et al, *J. Biol. Stand.*, 13:61–66 (1985). The test is performed by mixing serial dilutions of the toxoid or antigenic factor being tested with a suspension of $2 \times 10^4$ CHO cells in 200 µl culture broth in microtitre plates, allowing the cells to settle and grow at 37° C. for 2 days. At the end of the incubation, the clustering scores are recorded by microscopic examination. This test is sensitive to about 100 picograms of active toxin.

The results illustrated in TABLE 1 below show that treatment with formalin/amino acids alone yields complete inactivation, which however, is unstable and reverts to toxicity after 4 weeks at 37° C. Glutaraldehyde treatment alone yields incomplete, but stable inactivation. The process of the present invention, containing glutaraldehyde and formalin/amino acids treatment provides both complete and stable inactivation.

TABLE 1

Toxic Properties of Treated *B. pertussis* Toxin
CHO Cells Morphology Test

| Antigen Preparation | CPU/mcg | |
|---|---|---|
| | 30 d-4° C. | 30 d-37° C. |
| (1) Formalin-amino acids | <0.009* | 0.29 |
| (2) Glutaraldehyde | 0.13 | 0.13 |
| (3) Glutaraldehyde + Formalin/amino acids | <0.016* | <0.012* |

*Corresponds to the detection limit of the assay. 1 CPU (cytopathic unit) is the smallest dose of antigen which induces alteration of morphology of all the cells. For native toxin, 1 CPU corresponds to a concentration of about 3 ng/ml.

The study also involved a histamine sensitization test in mice with aluminum hydroxide adsorbed vaccine. Groups of 10 mice (Swiss OF1) are inoculated intravenously with one dose of vaccine, containing 6 µg of pertussis toxoid and 25 µg of treated FHA. After 4 days, the mice are challenged intraperitoneally with 1 mg histamine in buffered saline.

Two hours after challenge, the mortality rate of each group is recorded. See, e.g., Munoz et al, *Infect. Immunol.*, 33:820–826 (1981). The histamine test is sensitive to about 30 ng active toxin/mouse.

The results of this assay are shown in TABLE 2 and demonstrate, like the CHO test, that the formalin/amino acid treatment gave complete, but reversible inactivation upon incubation of the vaccine at 37° C. for one month. However, this test failed to detect toxicity or reversion to toxicity in both the glutaraldehyde and glutaraldehyde and formalin/amino acids treated preparations. This result is not contradictory to the CHO test results, because the histamine challenge test is less sensitive than the CHO test and does not detect the residual toxicity level in the glutaraldehyde treated samples.

TABLE 2

Toxic Properties of Adsorbed *B. pertussis* Vaccine Preparations
Histamine Sensitization Test in Mice

| Antigen Preparation | Mortality Rate | |
|---|---|---|
| | 30 d-4° C. | 30 d-37° C. |
| (1) Formalin-amino acids | 0/10 | 6/10 |
| (2) Glutaraldehyde | 0/10 | 0/10 |
| (3) Glutaraldehyde + Formalin | 0/10 | 0/10 |

EXAMPLE 3

Antigenic Properties of the Vaccine Component

The toxoid preparations obtained by inactivation with formalin/amino acid treatment alone, glutaraldehyde treatment alone or the method of the present invention as described in Example 1 were tested in an enzyme immunoassay using a specific rabbit antibody directed against PT. This antibody was obtained by immunizing rabbits with toxoid inactivated by formalin/amino acids.

This antibody was conjugated to biotin to allow detection of bound antibody by a streptavidin:peroxidase reagent, by determination of absorbance at 490 nm.

The results are illustrated in TABLE 3. They show that native toxin is most efficiently recognized. Toxoid prepared by glutaraldehyde inactivation alone shows the lowest reactivity. Toxoids prepared by formalin/amino acid treatment or by the treatment of the method of this invention display an intermediate reactivity.

TABLE 3

Antigenic Properties of Toxoided PT Reaction with Rabbit Anti-PT

| Antigen Preparation | D at 490 nm |
|---|---|
| Native toxin | 0.74 |
| Formalin/amino acids | 0.39 |
| Glutaraldehyde + formalin | 0.26 |
| Glutaraldehyde | 0.12 |

EXAMPLE 4

Protective Efficacy of Toxoided PT in Mice

Groups of 12 mice (Balb/c) were immunized by 2 μg of the toxoid preparations given twice at 7 days interval. 14 days after the second injection, they were challenged intranasally by a hypervirulent *B. pertussis* strain [(18–323 Ac+); See, e.g., Brezin et al., *FEMS Microbiol. Lett.*, 42:75–80 (1987)). Mortalities were recorded 6 days after challenge.

The results illustrated in TABLE 4 below show that the method of the invention provides a *B. pertussis* toxoid with the best protective efficacy.

TABLE 4

Protective Efficacy of Toxoided PT in Mice

| Antigen Preparation | no of deaths |
|---|---|
| None | 10 |
| Formalin/amino acids | 4 |
| Glutaraldehyde | 6 |
| Glutaraldehyde - formalin | 2 |

EXAMPLE 5

Vaccine Preparation

To formulate vaccines, *B. pertussis* antigens must be devoid of toxic properties, while retaining satisfactory immunological properties. This objective is accomplished by toxoiding *B. pertussis* toxin and/or by similar treatment applied to other antigens, which generally contain contaminating amounts of PT toxin. Treatment with glutaraldehyde as in U.S. Pat. No. 4,075,321 results in incomplete inactivation. Treatment with formalin alone as in European Patent Application No. 121,249 results in a complete but partially reversible inactivation and conserved immunogenicity. However, application of the method of this invention, e.g., treatment of the PT containing solution with glutaraldehyde and formalin/amino acids as herein described results surprisingly in both complete inactivation and irreversible inactivation. The resulting solution also is characterized by conserved immunogenicity. Thus, the products and processes of the present invention are valuable for their contributions to the safety and immunogenicity of *B. pertussis* vaccines containing these antigens.

EXAMPLE 6

Stability of the Vaccine Preparation

The vaccine preparation obtained by inactivation with the method of the present invention as described in Example 1 and the preparation procedure described in Example 5 were submitted to different heating treatments: one week at 56° C., 4 weeks at 37° C. or kept for 1 year at 4°–8° C. The vaccine samples were then assayed for active PT by the histamine sensitization assay in mice as described in Example 2. The results shown in Table 5 show the absence of reversion to toxicity after the above treatments.

TABLE 5

Toxic Properties of Adsorbed *B. pertussis* Vaccine Preparation
Histamine sensitization test in mice

| Preparation administered | Treatment | Dose | Mortality rate |
|---|---|---|---|
| solvent | | — | 0/10 |
| native PT | | 0.50 μg | 10/10 |
| | | 0.17 μg | 10/10 |
| | | 0.05 μg | 6/10 |
| vaccine | none | 25 μg | 0/10 |
| vaccine | 7 days, 56° C. | 25 μg | 0/10 |

TABLE 5-continued

Toxic Properties of Adsorbed *B. pertussis*
Vaccine Preparation
Histamine sensitization test in mice

| Preparation administered | Treatment | Dose | Mortality rate |
|---|---|---|---|
| vaccine | 28 days, 37° C. | 25 µg | 0/10 |
| vaccine | 1 year, 4–8° C. | 25 µg | 0/10 |

EXAMPLE 7

Immunogenicity and Stability upon Long Term Storage at 4°–8° C.

Antigen preparations, formulated as in example 5, were stored at 4°–8° C. and assayed at various times for the histamine sensitizing activity of PT as described in example 2 and for the ED50 of the immune response of Swiss OF1 mice to PT, i.e. the determination of the dose of inactivated PT needed to induce seroconversion of 50% of the mice. Similar tests were performed on adsorbed trivalent DTP vaccine, containing diphtheria toxoid, tetanus toxoid and the acellular pertussis vaccine components filamentous hemagglutinin and inactivated pertussis toxin prepared as described in example 1. The results (TABLE 6) show the absence of reversion and the absence of significant variations of the ED50.

TABLE 6

Immunogenicity and Stability Studies

| Vaccine Lot no | Storage at 4–8° C. (months) | HSF test mortality | ED50 ng/mouse |
|---|---|---|---|
| 306(1) | 0 | 0/10 | 42 |
|  | 10 | 0/10 | <103 |
|  | 27 | 0/10 | 42 |
| 310(1) | 0 | 0/10 | <103 |
|  | 10 | 0/10 | <103 |
|  | 27 | 0/10 | 46 |
| 353(2) | 0 | 0/10 | 69 |
|  | 15 | 0/10 | <103 |
|  | 27 | 0/10 | 58 |
| 354(2) | 0 | 0/10 | 50 |
|  | 15 | 0/10 | 152 |
|  | 27 | 0/10 | 80 |
| 355(2) | 0 | 0/10 | 76 |
|  | 15 | 0/10 | <103 |
|  | 27 | 0/10 | 45 |

(1) Inactivated PT, 25 µg.

(2) Trivalent DTP (diphtheria toxoid, tetanus toxoid, *B. pertussis* filamentous hemagglutinin (FHA) and inactivated PT, 25 µg).

The method of the present invention may be applied to other antigens, such as diphtheria toxin, tetanus toxin and the like. Such modifications and alterations to the compositions and processes of the present invention are intended to be encompassed in the scope of the claims appended hereto.

We claim:

1. A method for the detoxification of Bordetella toxin from a partially or extensively purified preparation containing said toxin comprising treating said preparation with glutaraldehyde to partially detoxify said toxin, and reacting the partially detoxified toxin with formalin in the presence of amino acids selected from the group consisting of tryptophan, glycine, lysine and N-acetyl-tryptophan.

2. The method according to claim 1 wherein said toxin is *Bordetella pertussis* toxin.

3. The method according to claim 2 wherein said glutaraldehyde treatment comprises treating an aqueous solution containing said antigen at a concentration of between 0.02 to 2 mg/ml with from 0.03 to 0.07% of 25% aqueous glutaraldehyde solution by weight.

4. The method according to claim 3 wherein said formalin and amino acid treatment comprises adding to said glutaraldehyde treated antigen solution between 0.05 to 2% by weight of at least one selected amino acid and between 1 to 10% by weight formalin, maintaining said solution at a temperature of between 37° to 45° C.

5. The method according to claim 4 further comprising optionally subjecting the solution to ultrasonication to remove aggregates formed during detoxification.

6. The method according to claim 4 comprising dialyzing the solution to remove excess reagent, wherein the residual formalin concentration is always below 200 ppm in said solution.

7. A *B. pertussis* toxin detoxified by the method of claim 2.

8. A vaccine comprising an immunogenic amount of the detoxified *B. pertussis* toxin of claim 7.

\* \* \* \* \*